(12) United States Patent
Parascandola et al.

(10) Patent No.: US 7,729,757 B2
(45) Date of Patent: Jun. 1, 2010

(54) CORRECTIVE VOICE PROMPTS FOR CAREGIVING DEVICE

(75) Inventors: Michael Parascandola, Londonderry, NH (US); Marc Cordaro, Sudbury, MA (US); Suzanne Crowell, Beverly, MA (US); Gary A. Freeman, Newton Center, MA (US)

(73) Assignee: ZOLL Medical Corporation, Chelmsford, MA (US)

( * ) Notice: Subject to any disclaimer, the term of this patent is extended or adjusted under 35 U.S.C. 154(b) by 618 days.

(21) Appl. No.: 10/952,451

(22) Filed: Sep. 28, 2004

(65) Prior Publication Data

US 2005/0251214 A1 Nov. 10, 2005

Related U.S. Application Data

(63) Continuation-in-part of application No. 10/841,367, filed on May 7, 2004.

(51) Int. Cl.
*A61N 1/39* (2006.01)
(52) U.S. Cl. .............................................. 607/2; 607/5
(58) Field of Classification Search ..................... 607/5, 607/6, 33, 142
See application file for complete search history.

(56) References Cited

U.S. PATENT DOCUMENTS

| | | |
|---|---|---|
| 4,019,501 A | 4/1977 | Harris |
| 4,077,400 A | 3/1978 | Harrigan |
| 4,095,590 A | 6/1978 | Harrigan |
| 4,588,383 A | 5/1986 | Parker et al. |
| 4,610,254 A | 9/1986 | Morgan et al. |
| 4,863,385 A | 9/1989 | Pierce |
| 5,137,458 A | 8/1992 | Ungs et al. |
| 5,285,792 A | 2/1994 | Sjoquist et al. |
| 5,496,257 A | 3/1996 | Kelly |
| 5,662,690 A | 9/1997 | Cole et al. |
| 5,700,281 A | 12/1997 | Brewer et al. |
| 5,792,190 A | 8/1998 | Olson et al. |
| 5,913,685 A | 6/1999 | Hutchins |
| 5,955,956 A | 9/1999 | Stendahl et al. |
| 6,125,299 A | 9/2000 | Groenke et al. |
| 6,306,107 B1 | 10/2001 | Myklebust et al. |

(Continued)

OTHER PUBLICATIONS

Cummins et al., Defibrillator Failures: Causes and Problems and Recommendations for Improvement, JAMA, vol. 264, No. 8 (1990).

(Continued)

*Primary Examiner*—Carl H Layno
*Assistant Examiner*—Brian T Gedeon
(74) *Attorney, Agent, or Firm*—Fish & Richardson P.C.

(57) ABSTRACT

A medical device such as a defibrillator that incorporates corrective voice prompts that navigate users around operator errors. The voice prompts may, for example, address errors of readiness (e.g., failing to connect the defibrillator to an AC power source, failing to pre-connect electrodes, etc.), errors of omission (i.e., forgetting to do something, such as attempting to deliver a shock before the defibrillator is charged), and errors of commission (i.e., doing the wrong thing, such as attempting to shock VF when in the synchronization mode). The voice prompts may address errors in the delivery of therapy (e.g., attempting to shock VF when in the synchronization mode) or they may address errors other than in the delivery of therapy (e.g., failing to connect to an AC power source).

7 Claims, 5 Drawing Sheets

U.S. PATENT DOCUMENTS

| | | |
|---|---|---|
| 6,334,070 B1 | 12/2001 | Nova et al. |
| 6,356,785 B1 * | 3/2002 | Snyder et al. .................. 607/5 |
| 6,370,428 B1 * | 4/2002 | Snyder et al. .................. 607/5 |
| 6,390,996 B1 | 5/2002 | Halperin et al. |
| 6,405,082 B1 | 6/2002 | Borgenicht |
| 6,697,671 B1 | 2/2004 | Nova et al. |
| 6,827,695 B2 * | 12/2004 | Palazzolo et al. ............. 601/41 |
| 2002/0007832 A1 | 1/2002 | Doherty |
| 2003/0004547 A1 | 1/2003 | Owen et al. |
| 2003/0036044 A1 | 2/2003 | Pastrick et al. |
| 2003/0055458 A1 | 3/2003 | Hamilton et al. |
| 2003/0083699 A1 | 5/2003 | Hamilton et al. |
| 2003/0216785 A1 * | 11/2003 | Edwards et al. ................ 607/5 |
| 2005/0070964 A1 * | 3/2005 | Hansen et al. ................. 607/5 |

OTHER PUBLICATIONS

Part 4: The Automated External Defibrillator: Key Link in the Chain of Survival, Circulation 102:60-76 (2000).

* cited by examiner

| Error in failing to charge the defibrillator's battery. |
|---|
| Error in failing to connect the unit to AC power. |
| Errors associated with the storage, management, deletion, transmission, or correction of information. E.g., errors associated with the use of removable forms of media. E.g., errors associated with the use of wired or wireless transmission of data. |
| Errors associated with recording, displaying, storing, or printing of electrocardiographic (ECG) data. |
| Errors related to analysis of electrocardiographic (ECG) data. |
| Errors associated with vital signs monitoring. E.g., heart rate, temperature, blood pressure (non-invasive and invasive), pulse oximetry, end tidal CO2, respiration, blood gases, CO, or blood chemistries. |
| E.g., errors in calibration, sensor replacement, environmental issues (i.e. high ambient lighting), or cable placement. |

Examples of Errors Relating to Other Than Delivery of Therapy

FIG. 7

| Errors relating to delivery of defibrillation. E.g., error in failing to select the defibrillation mode. |
|---|
| Errors relating to delivery of transcutaneous pacing. E.g., errors relating to increasing or decreasing pacing rate. |
| Error in selecting synchronized delivery of electrical stimulation during a cardiac arrest situation. |

Examples of Errors Relating to Delivery of Therapy

FIG. 8

CORRECTIVE VOICE PROMPTS FOR CAREGIVING DEVICE

CROSS-REFERENCE TO RELATED APPLICATIONS

This application is a continuation in part of U.S. application Ser. No. 10/841,367, filed on May 7, 2004, and entitled, "Automated Caregiving Device with Prompting Based on Caregiver Progress" (incorporated herein by reference).

BACKGROUND

Defibrillators and defibrillator-external pacemakers are employed to restore and maintain a heart's normal rhythm in either an emergency situation such as cardiac arrest, or voluntarily to normalize a person's rhythm in non-life threatening situations (e.g., atrial fibrillation).

Use of a defibrillator requires specific certification resulting from such programs as the American Heart Association's Advanced Life or Base Life Support courses. Further institutional or organizational training or competency evaluation may also be required. These requirements generally remain true for both manual and semi-automatic (AED) defibrillators. In order to maximize familiarity with this lifesaving equipment, institutions and organizations generally require periodic recertification and or demonstration of competency. In part, these training requirements are an attempt to maximize an operator's chance of successfully using a defibrillator.

Use of a defibrillator, particularly in emergency situations, places a great deal of stress on its operator. As such, even trained users still make mistakes when trying to operate a defibrillator. At least one study has demonstrated that upwards of 50 percent of defibrillator failures can be attributed to operator errors. Failure to use the defibrillator correctly can cause delays and compromise therapy. Bone, *Defibrillator Failures: Causes and Problems and Recommendations for Improvement*, JAMA, Vol. 264, No. 8 (1990).

Another factor contributing to operator errors is that many institutions and organizations possess different models of defibrillators that employ different operating interfaces, terminology, etc. The difference in operating systems can cause delays and mistakes, both of which may compromise therapy.

Operators are generally required to perform daily test and maintenance on a defibrillator. Such activities may require operation from a DC (battery) source that leads one to disconnect the defibrillator from AC power source. It is not beyond reason that an operator, after completing a daily test might leave the defibrillator in the powered on condition, and not connect to the AC power source. Such conditions would drain the battery and render the defibrillator therapeutically useless. Another such example might be the disconnecting of therapeutic electrodes for daily test purposes. If not reconnected, delays might result that compromise therapy.

The current state of the art employs visual prompts or nonspecific tones to communicate user errors, and/or communicate corrective actions to defibrillator operators. FIG. 6 gives an example of a prior art visual prompt for communicating a user error. A recognized shortcoming of visual prompts is that they can be easily overlooked under the stress of an emergency situation. They are passive as this approach relies on an operator looking specifically at the display field at all times. Newer AED defibrillators have taken the step of incorporating graphic prompts or icons into the physical design and labeling of the product in order to give them more permanency.

In an attempt to overcome these shortcomings, some defibrillators have incorporated a variety of high and low pitched tones as alert alarms to draw attention to the device. Initially successful, their shortcoming has become a lack of specificity. Over the years there has been proliferation of tonal alarms on a variety of medical equipment likely to be present in an emergency resuscitation. Further, the growing trend toward incorporating more vital sign parameters into pre-hospital defibrillators also raises the number of warning tones rescuers must decipher.

In recent years voice prompts have been employed to simplify the therapeutic use of defibrillators. That is they guide users, some minimally trained, through the setup and use of a defibrillator for delivery of a potentially lifesaving electrical shock (e.g., attaching electrodes, prompting need for CPR, and shock delivery). Most recently, defibrillators have begun to expand the range of the voice prompting to include the ABCs (airway, breathing, chest compressions) of resuscitation, and to provide feedback on the quality and rate of chest compressions. Olson U.S. Pat. No. 5,792,190 and Edward U.S. Application No. 2003/0216785 describe the use of voice prompts as part of an AED interface; they generally describe the role of voice prompts as instructions for a series of operations performed by the operator for the treatment of a patient, including the deployment and use of an AED. Nova U.S. Pat. Nos. 6,334,070 and 6,697,671 and Snyder U.S. Pat. No. 6,356,785 expand the use of therapeutic voice prompts to include BLS and ALS treatment protocols; operational faults are communicated to the operator by visual indicators (e.g., LED) or non-specific tonal sounds. Stendahl U.S. Pat. No. 5,955,956 describes the use of an audible alarm system in an AED in response to processor detected faults that are found during a periodic self-test. Borgenicht U.S. Pat. No. 6,405,082 describes the use of tonal and verbal prompts to confirm the therapeutic modes of a defibrillator, i.e., to alert the operator that the defibrillation mode has been selected, or that one is charging for synchronized cardioversion.

SUMMARY

In general, the invention features a medical caregiving device (e.g., a defibrillator) that incorporates corrective voice prompts that navigate users around operator errors. The voice prompts may, for example, address errors of readiness (e.g., failing to connect the defibrillator to an AC power source, failing to pre-connect electrodes, etc.), errors of omission (i.e., forgetting to do something, such as attempting to deliver a shock before the defibrillator is charged), and errors of commission (i.e., doing the wrong thing, such as attempting to shock VF when in the synchronization mode). The voice prompts may address errors in the delivery of therapy (e.g., attempting to shock VF when in the synchronization mode) or they may address errors other than in the delivery of therapy (e.g., failing to connect to an AC power source).

In general the invention features a medical device of the type used for assisting a user in delivering therapy to a patient, the device comprising a user interface including a speaker configured to deliver voice prompts to a user to assist the user in operating the device; at least one sensor or circuit element configured to detect an error made by the user in operating the device; a memory in which a plurality of different voice prompts are stored; a processor configured to determine which of the different voice prompts should be selected for delivery based on the detected error; and circuitry configured to work with the memory and the user interface and speaker to deliver the selected voice prompt.

In preferred implementations, one or more of the following features may be incorporated. The device may include a defibrillator. The selected voice prompts may address errors in the delivery of therapy, or they may address errors other than errors in the delivery of therapy. The voice prompts may include a prompt to correct the user's error in failing to select the defibrillation mode. The voice prompts may include a prompt to correct the user's error in selecting synchronized delivery of electrical stimulation during a cardiac arrest situation. The voice prompts may include a prompt to correct the user's error in failing to charge the defibrillator's battery. The voice prompts may include a prompt to correct the operator's failure to connect the device to AC power. The voice prompts may include a prompt to correct operator errors associated with the storage, management, deletion, transmission, or correction of information. The voice prompts may include a prompt to correct operator errors associated with the use of removable forms of media. The voice prompts may include a prompt to correct operator errors associated with the use of wired or wireless transmission of data. The voice prompts may include a prompt to correct operator errors associated with recording, displaying, storing, or printing of electrocardiographic (ECG) data. The voice prompts may include a prompt to correct operator errors related to analysis of electrocardiographic (ECG) data. The voice prompts may include a prompt to correct operator errors associated with vital signs monitoring. The vital signs monitoring may comprise one or more of the following: heart rate, temperature, blood pressure (non-invasive and invasive), pulse oximetry, end tidal $CO_2$, respiration, blood gases, CO, or blood chemistries. The voice prompts may include a prompt relating to errors in calibration, sensor replacement, environmental issues (i.e. high ambient lighting), or cable placement. The voice prompts may include a prompt to correct operator errors associated with transcutaneous pacing. The voice prompts may include a prompt relating to increasing or decreasing pacing rate.

Providing voice prompts rather than audible tones or visual information on a display provides a much more effective means of informing the user of an error, and of informing him of how to correct that error. The voice prompts get the attention of the user, and they are more effective at getting the user to take appropriate action.

Other features and advantages of the invention will be found in the detailed description, drawings, and claims.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 7 is a table listing examples of non-therapy-delivery errors for which voice prompts could be delivered FIG. 8 is a table listing examples of therapy-delivery errors for which voice prompts could be delivered.

DETAILED DESCRIPTION

There are a great many possible implementations of the invention, too many to describe herein. Some possible implementations that are presently preferred are described below. It cannot be emphasized too strongly, however, that these are descriptions of implementations of the invention, and not descriptions of the invention, which is not limited to the detailed implementations described in this section but is described in broader terms in the claims.

Figure 1:
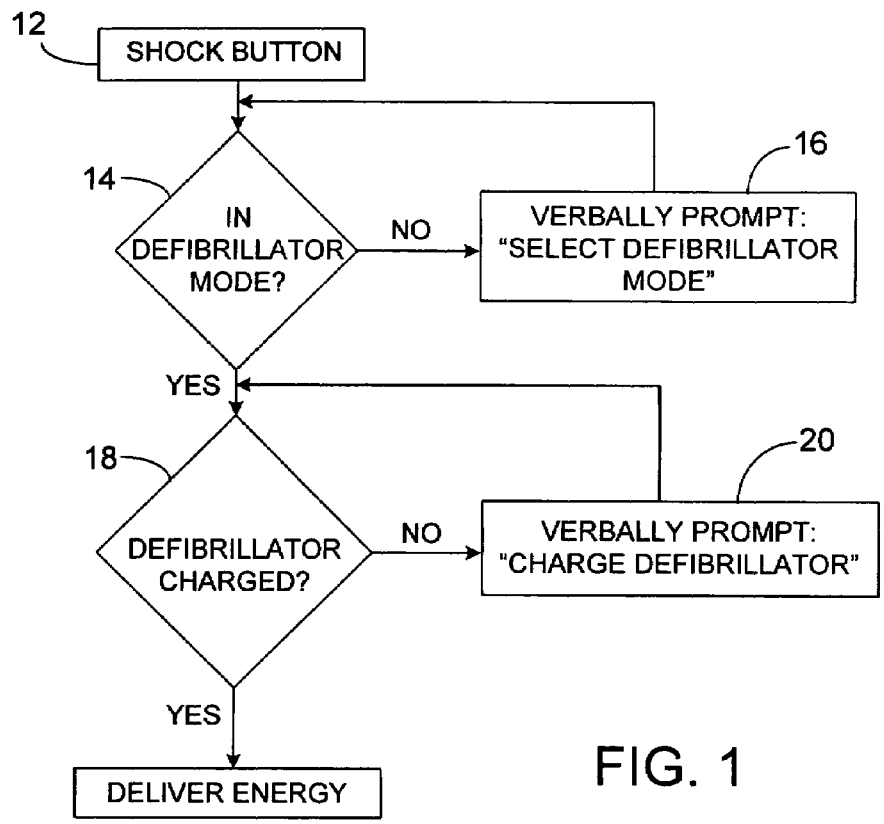
FIG. 1 is a block diagram illustrating one implementation of the invention.

FIG. 1 depicts one possible manner in which voice prompts may be used to correct operator errors of a type that could generally be called errors of omission. In this implementation, the operator presses (12) the button designated for shock delivery. The microprocessor controlled logic initially detects (14) whether the defibrillator is in the defibrillator mode (e.g., it may be in the pacing mode). If it is not in the defibrillator mode, a voice prompt is delivered (16) to the operator to "Select the Defibrillator Mode." Alternately, the defibrillator mode may have already been selected, but the operator may have failed to charge the defibrillator. If this is detected (18), the defibrillator may prompt (20) the operator to "Press the Charge Button." The same approach may be applied to the pacing mode, to cardioversion, and to other applications.

Figure 2:
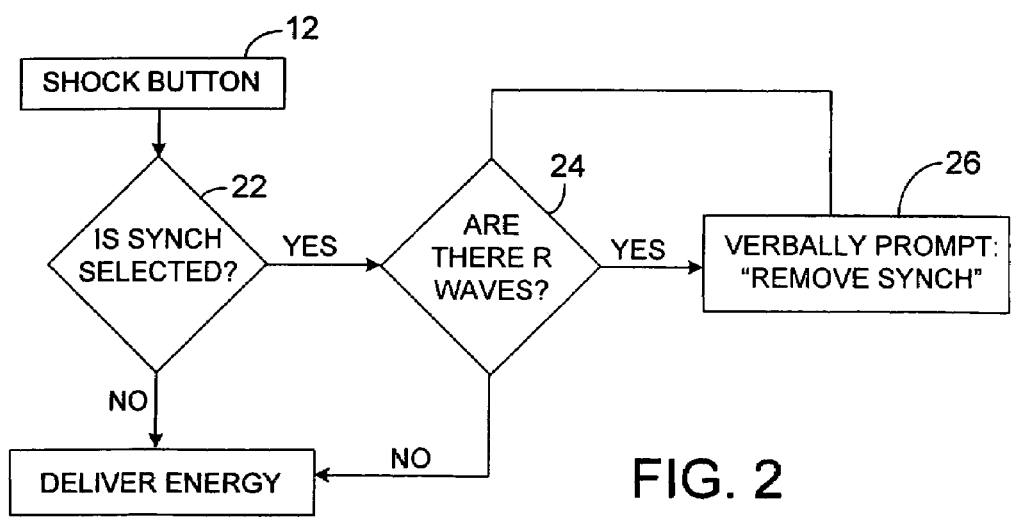
FIG. 2 is a block diagram illustrating a second implementation of the invention.

FIG. 2 depicts another implementation, in which voice prompts are used to correct operator errors of a type that could generally be called errors of commission. In this implementation, the defibrillator prompts the operator (22) regarding a user-created problem that blocks the delivery of therapy. For example, if the synchronization mode is erroneously activated during the treatment of a cardiac arrest condition, the depicted logic and resulting voice prompt will guide the operator around the self-generated problem. If the logic has determined that the synchronization mode has been selected, it then determines (24) whether there are R waves present. If so, then it may prompt (26) the operator to remove the synchronization selection.

Figure 3:
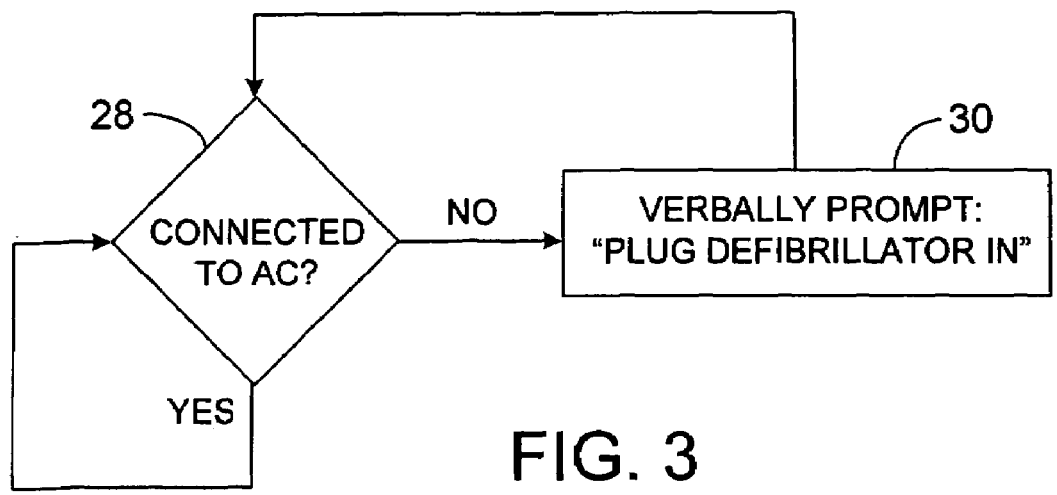
FIG. 3 is a block diagram illustrating a third implementation of the invention.
Figure 6:
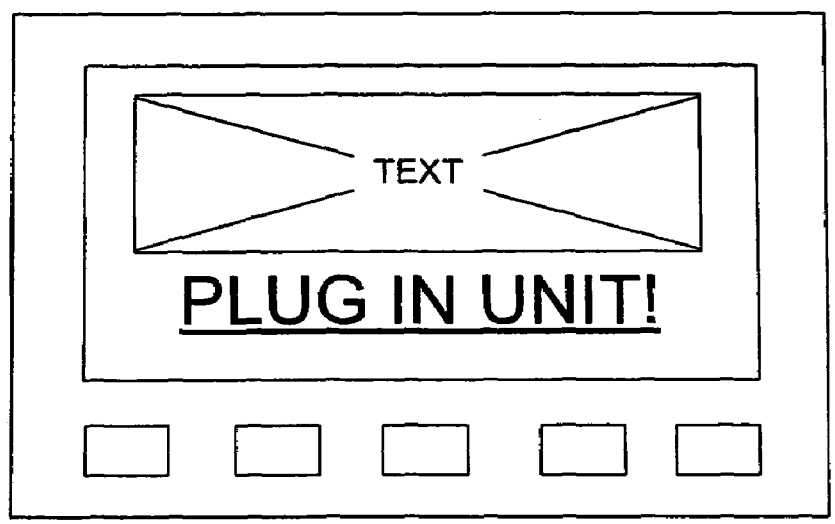
FIG. 6 is a view of a prior art defibrillator display showing a visual prompt for communicating an error to a user.

FIG. 3 depicts the concept of a "sentinel" that continuously monitors critical defibrillator functions and operations; this implementation could be regarded as assisting in correction of readiness errors. In this implementation, the logic monitors (28) the connection to an AC power source. If the defibrillator were to be left unplugged, the defibrillator could prompt (30) "Plug Defibrillator In." Further, as the criticality of a situation increased, it could change the content of the voice prompt and/or the frequency of the prompt.

Other examples of errors that could be corrected by voice prompts include: (1) the operator's failure to insert a memory card into the device; (2) the operator's failure to make an online connection prior to attempting to send data; (3)

Preferably, a voice prompt does more than alert the user of an error; it goes on to instruct the user as to the corrective action that needs to be taken.

Figure 4:
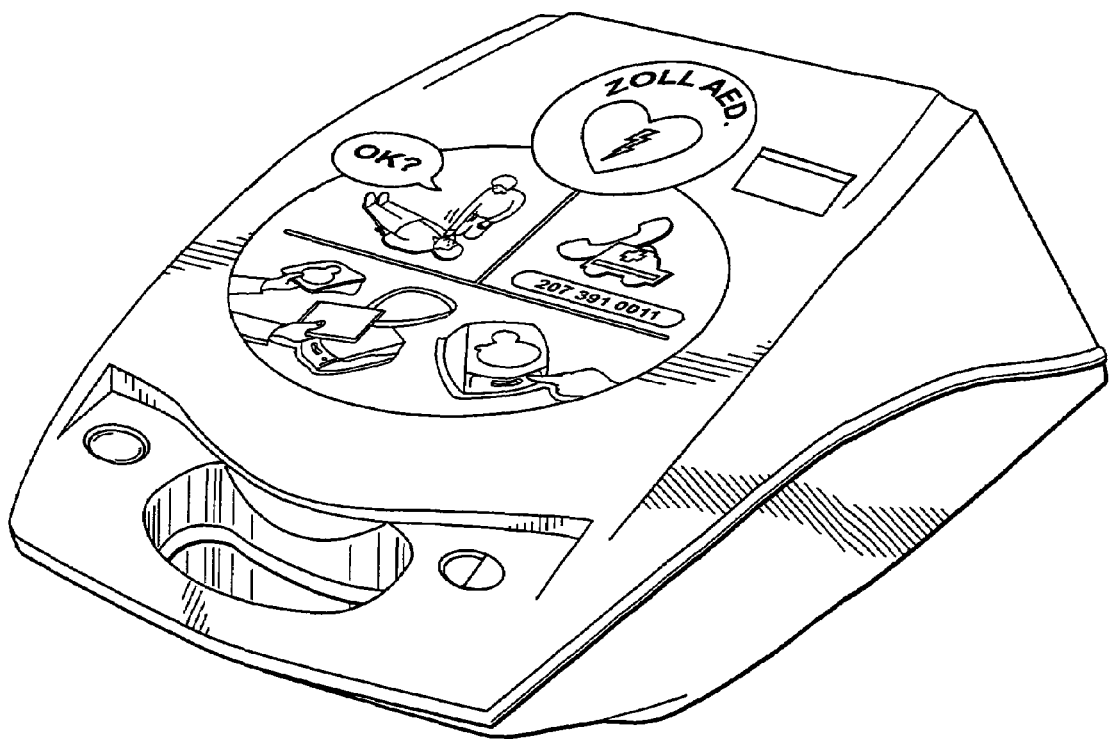
FIG. 4 is a perspective view of an automatic external defibrillator (AED) of a type that could incorporate one or more implementations of the invention.

FIG. 4 shows the exterior of an automatic external defibrillator 10 of a type that might incorporate the voice prompts disclosed herein.

Figure 5:
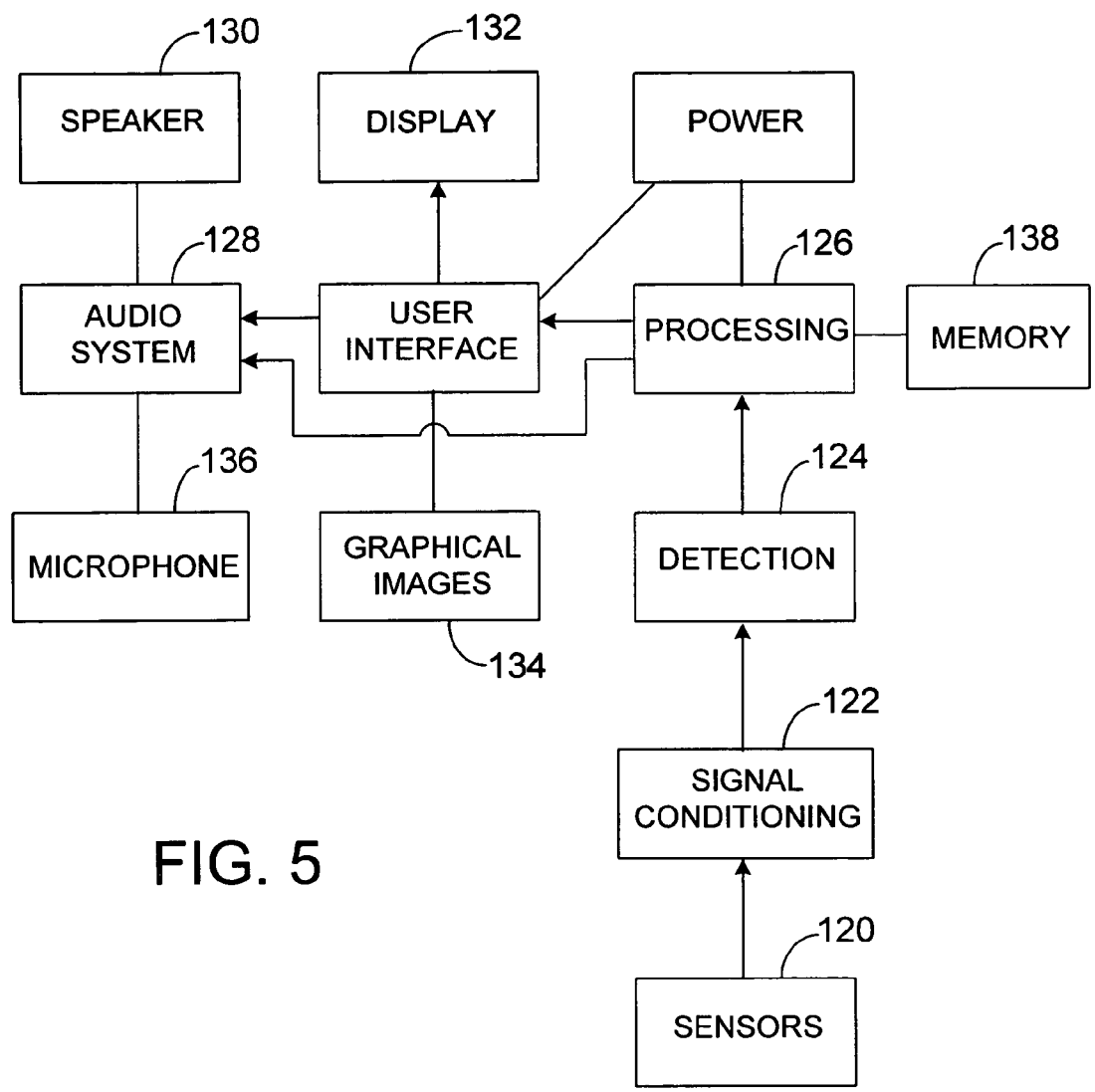
FIG. 5 is a block diagram of at least a portion of an AED implementation.

FIG. 5 shows some of the basic functional blocks that would be implemented in an external defibrillator (e.g., an AED) that incorporated the implementations disclosed herein. Sensors 120 with associated signal conditioning 122 and detection circuitry 124 provide information to a processing unit 126 as to errors that have occurred. The processor uses the information to direct an audio system 128 to deliver voice prompts (which are stored in memory 138) from a speaker 130. The processor may also cause information to be presented on a display 132 or draw the user's attention to graphical images 134 (e.g., by lighting up the images or activating lights adjacent to the images). A microphone 136 may be used to record information during an event.

FIGS. 7-8 are tables listing examples of non-therapy-delivery errors for which voice prompts could be delivered (FIG. 7) and therapy-delivery errors for which voice prompts could be delivered (FIG. 8) As the table indicates, the voice prompts may include prompts for correcting a wide variety of errors. The voice prompts may include a prompt to correct the user's error in failing to select the defibrillation mode. The voice prompts may include a prompt to correct the user's error in selecting synchronized delivery of electrical stimulation during a cardiac arrest situation. The voice prompts may include a prompt to correct the user's error in failing to charge the defibrillator's battery. The voice prompts may include a prompt to correct the operator's failure to connect the device to AC power. The voice prompts may include a prompt to correct operator errors associated with the storage, management, deletion, transmission, or correction of information. The voice prompts may include a prompt to correct operator errors associated with the use of removable forms of media. The voice prompts may include a prompt to correct operator errors associated with the use of wired or wireless transmission of data. The voice prompts may include a prompt to correct operator errors associated with recording, displaying, storing, or printing of electrocardiographic (ECG) data. The voice prompts may include a prompt to correct operator errors related to analysis of electrocardiographic (ECG) data. The voice prompts may include a prompt to correct operator errors associated with vital signs monitoring. The vital signs monitoring may comprise one or more of the following: heart rate, temperature, blood pressure (non-invasive and invasive), pulse oximetry, end tidal $CO_2$, respiration, blood gases, CO, or blood chemistries. The voice prompts may include a prompt relating to errors in calibration, sensor replacement, environmental issues (i.e. high ambient lighting), or cable placement. The voice prompts may include a prompt to correct operator errors associated with transcutaneous pacing. The voice prompts may include a prompt relating to increasing or decreasing pacing rate.

Many other implementations of the invention other than those described above are within the invention, which is defined by the following claims. For example, the invention can be applied to external defibrillators of the type used within the hospital as well as outside the hospital.

What is claimed is:

1. A medical device of the type used for assisting a user in delivering therapy to a patient, the device comprising
   a user interface including a speaker configured to deliver voice prompts to a user to assist the user in operating the device;
   at least one sensor or circuit element configured to detect an error made by the user in the manner in which the user operates the device, the error comprising the operator's failure to connect the device to AC power
   a memory in which a plurality of different voice prompts are stored;
   a processor configured to determine which of the different voice prompts should be selected for delivery based on the detected error; and
   circuitry configured to work with the memory and the user interface and speaker to deliver the selected voice prompt to assist the user in correcting the error.

2. A medical device of the type used for assisting a user in delivering therapy to a patient, the device comprising
   a user interface including a speaker configured to deliver voice prompts to a user to assist the user in operating the device;
   at least one sensor or circuit element configured to detect an error made by the user in the manner in which the user operates the device, the error comprising operator errors associated with the storage, management, deletion, transmission, or correction of information;
   a memory in which a plurality of different voice prompts are stored;
   a processor configured to determine which of the different voice prompts should be selected for delivery based on the detected error; and
   circuitry configured to work with the memory and the user interface and speaker to deliver the selected voice prompt to assist the user in correcting the error.

3. A medical device of the type used for assisting a user in delivering therapy to a patient, the device comprising
   a user interface including a speaker configured to deliver voice prompts to a user to assist the user in operating the device;
   at least one sensor or circuit element configured to detect an error made by the user in the manner in which the user operates the device, the error comprising operator errors associated with the use of removable forms of media,
   a memory in which a plurality of different voice prompts are stored;
   a processor configured to determine which of the different voice prompts should be selected for delivery based on the detected error; and
   circuitry configured to work with the memory and the user interface and speaker to deliver the selected voice prompt to assist the user in correcting the error.

4. A medical device of the type used for assisting a user in delivering therapy to a patient, the device comprising
   a user interface including a speaker configured to deliver voice prompts to a user to assist the user in operating the device;
   at least one sensor or circuit element configured to detect an error made by the user in the manner in which the user operates the device, the error comprising operator errors associated with the use of wired or wireless transmission of data,
   a memory in which a plurality of different voice prompts are stored;
   a processor configured to determine which of the different voice prompts should be selected for delivery based on the detected error; and
   circuitry configured to work with the memory and the user interface and speaker to deliver the selected voice prompt to assist the user in correcting the error.

5. A medical device of the type used for assisting a user in delivering therapy to a patient, the device comprising
   a user interface including a speaker configured to deliver voice prompts to a user to assist the user in operating the device;
   at least one sensor or circuit element configured to detect an error made by the user in the manner in which the user operates the device, the error comprising operator errors associated with recording, displaying, storing, or printing of electrocardiographic (ECG) data,
   a memory in which a plurality of different voice prompts are stored;
   a processor configured to determine which of the different voice prompts should be selected for delivery based on the detected error; and circuitry configured to work with the memory and the user interface and speaker to deliver the selected voice prompt to assist the user in correcting the error.

6. A medical device of the type used for assisting a user in delivering therapy to a patient, the device comprising
- a user interface including a speaker configured to deliver voice prompts to a user to assist the user in operating the device;
- at least one sensor or circuit element configured to detect an error made by the user in the manner in which the user operates the device, the error comprising operator errors related to analysis of electrocardiographic (ECG) data,
- a memory in which a plurality of different voice prompts are stored;
- a processor configured to determine which of the different voice prompts should be selected for delivery based on the detected error; and
- circuitry configured to work with the memory and the user interface and speaker to deliver the selected voice prompt to assist the user in correcting the error.

7. A medical device of the type used for assisting a user in delivering therapy to a patient, the device comprising
- a user interface including a speaker configured to deliver voice prompts to a user to assist the user in operating the device;
- at least one sensor or circuit element configured to detect an error made by the user in the manner in which the user operates the device, the error comprising one or more errors in calibration, sensor replacement, environmental issues (ambient lighting) or cable placement,
- a memory in which a plurality of different voice prompts are stored;
- a processor configured to determine which of the different voice prompts should be selected for delivery based on the detected error; and
- circuitry configured to work with the memory and the user interface and speaker to deliver the selected voice prompt to assist the user in correcting the error.

* * * * *

UNITED STATES PATENT AND TRADEMARK OFFICE
CERTIFICATE OF CORRECTION

PATENT NO. : 7,729,757 B2  Page 1 of 1
APPLICATION NO. : 10/952451
DATED : June 1, 2010
INVENTOR(S) : Michael Parascandola et al.

It is certified that error appears in the above-identified patent and that said Letters Patent is hereby corrected as shown below:

Column 8, line 10, "(ambient lighting)" should be --ambient lighting,--.

Signed and Sealed this

Sixteenth Day of November, 2010

David J. Kappos
*Director of the United States Patent and Trademark Office*